US007695987B2

(12) United States Patent
Davis et al.

(10) Patent No.: US 7,695,987 B2
(45) Date of Patent: Apr. 13, 2010

(54) METHOD FOR AUTOMATIC DETERMINATION OF SEMICONDUCTOR PLASMA CHAMBER MATCHING AND SOURCE OF FAULT BY COMPREHENSIVE PLASMA MONITORING

(75) Inventors: Matthew F. Davis, Brookdale, CA (US); Lei Lian, Santa Clara, CA (US)

(73) Assignee: Applied Materils, Inc., Santa Clara, CA (US)

( * ) Notice: Subject to any disclaimer, the term of this patent is extended or adjusted under 35 U.S.C. 154(b) by 0 days.

(21) Appl. No.: 11/612,961

(22) Filed: Dec. 19, 2006

(65) Prior Publication Data

US 2007/0095789 A1   May 3, 2007

Related U.S. Application Data

(63) Continuation of application No. 10/628,001, filed on Jul. 25, 2003, now Pat. No. 7,169,625.

(51) Int. Cl.
H01L 21/00   (2006.01)
(52) U.S. Cl. .......................................................... 438/9
(58) Field of Classification Search ...................... 438/5, 438/7, 10–11, 16–18, 22–24, 29, 31, 34–36, 438/128–130, 149, 484, 538
See application file for complete search history.

(56) References Cited

U.S. PATENT DOCUMENTS

| 2,942,328 | A | * | 6/1960 | Bowne et al. | 438/10 |
| 3,396,059 | A | * | 8/1968 | Giammanco | 117/42 |
| 5,986,747 | A | * | 11/1999 | Moran | 356/72 |
| 6,021,215 | A | * | 2/2000 | Kornblit et al. | 382/141 |
| 6,419,846 | B1 | | 7/2002 | Toprac et al. | |
| 6,420,194 | B1 | * | 7/2002 | Reitman | 438/9 |
| 6,521,080 | B2 | | 2/2003 | Balasubramhanya et al. | |
| 6,714,833 | B2 | * | 3/2004 | Nakano et al. | 700/121 |
| 6,864,109 | B2 | * | 3/2005 | Chang et al. | 438/16 |
| 2002/0132380 | A1 | * | 9/2002 | Nakano et al. | 438/14 |
| 2005/0019961 | A1 | * | 1/2005 | Davis et al. | 438/7 |
| 2005/0019964 | A1 | * | 1/2005 | Chang et al. | 438/16 |

OTHER PUBLICATIONS

Yue, et al., "Plasma etching endpoint detection using multiple wavelengths for small open-area wafers," J. Vac. Sci. Technol. A, 19(1), Jan./Feb. 2001, 66-75.

* cited by examiner

Primary Examiner—Charles D Garber
Assistant Examiner—Andre' C Stevenson
(74) Attorney, Agent, or Firm—Patterson & Sheridan, LLP

(57) ABSTRACT

A method and apparatus for automatic determination of semiconductor plasma chamber matching a source of fault are provided. Correlated plasma attributes are measured for process used for calibration both in a chamber under study and in a reference chamber. Principal component analysis then is performed on the measured correlated attributes so as to generate steady principal components and transitional principal components; and these principal components are compared to reference principal components associated with a reference chamber. The process used for calibration includes a regular plasma process followed by a process perturbation of one process parameter. Similar process perturbation runs are conducted several times to include different perturbation parameters. By performing inner products of the principal components of chamber under study and the reference chamber, matching scores can be reached. Automatic chamber matching can be determined by comparing these scores with preset control limits. The potential source(s) of chamber fault can also be identified by the lowest matching score(s).

15 Claims, 11 Drawing Sheets

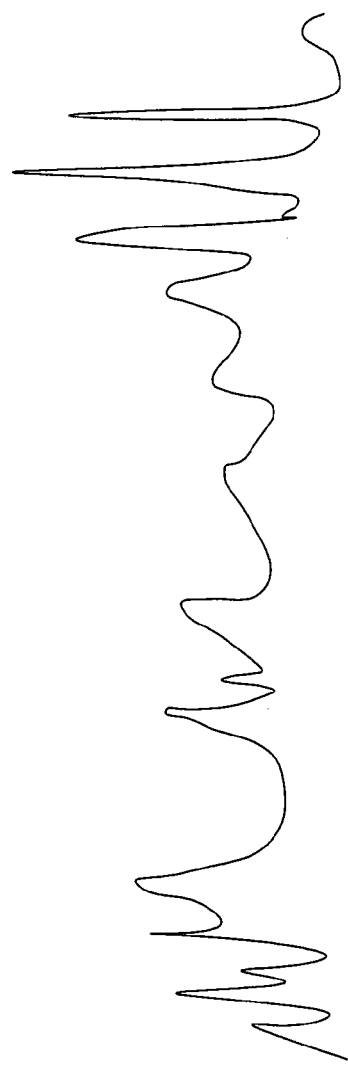
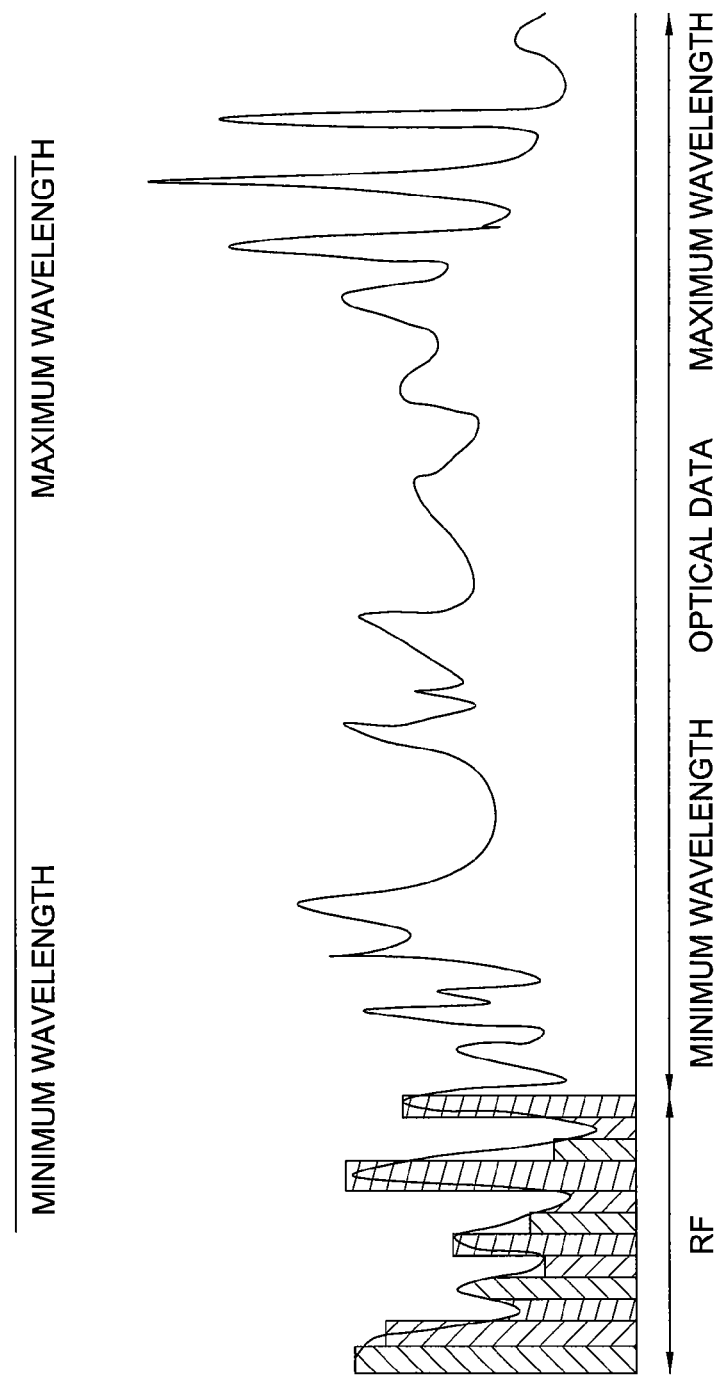
FIG. 3
FIG. 5

METHOD FOR AUTOMATIC DETERMINATION OF SEMICONDUCTOR PLASMA CHAMBER MATCHING AND SOURCE OF FAULT BY COMPREHENSIVE PLASMA MONITORING

CROSS-REFERENCE TO RELATED APPLICATION

This application is a continuation of U.S. patent application Ser. No. 10/628,001, filed Jul. 25, 2003 now U.S. Pat. No. 7,169,625, which is incorporated by reference in its entirety.

BACKGROUND OF THE INVENTION

1. Field of the Invention

The present invention relates to semiconductor substrate processing systems. More particularly, the present invention relates to techniques and apparatus for automatically determining whether a substrate process chamber matches a reference substrate process chamber and the potential source(s) of chamber fault.

2. Description of the Related Art

Within the semiconductor industry, an ever present need exists for improved process repeatability and control. As new generations of integrated circuits employ smaller feature sizes than were contemplated in previous generations, greater demands are placed on the integrated circuit fabrication process. Deposition and etching one or more layers of a semiconductor substrate in a plasma environment are two of the most common steps in integrated circuit manufacturing. To ensure that a correct quantity and quality of film is deposited or etched, the plasma state of the process chamber needs to be monitored comprehensively prior to, during and after production substrate processing. Comprehensive chamber monitoring prior to production substrate processing allows proper chamber qualification to be conducted. Comprehensive chamber monitoring during production substrate processing allows correct endpoint and fault detection. Comprehensive chamber monitoring after production substrate processing allows diagnosis of source of fault, if faults were detected during substrate processing.

To ensure that a correct amount and quality of film is deposited or etched, substrate processing in a process chamber needs to be monitored during the processing. Plasma state of the process and chamber during processing needs to match that of a selected process in a "reference" chamber to ensure the chamber and process are functioning as expected and also correct endpoint detection can occur to terminate the process at the desired time. If the plasma state of the process and chamber during processing does not match that of a selected process in a "reference"chamber, a potential fault is detected and the operator is alarmed to take appropriate action. Details of how a chamber and process can be monitored during process to detect endpoint and fault have been disclosed in commonly assigned U.S. Pat. No. 6,368,975, entitled "Method and Apparatus For Monitoring A Process By Employing Principal component Analysis", issued on Apr. 9, 2002 and its divisional application Ser. No. 10/341,696, filed on Jan. 14, 2003.

To ensure that a correct amount and quality of film is deposited or etched,substrate processing in a process chamber needs to be monitored during the processing. Plasma state of the process and chamber during processing needs to match that of a selected process in a "reference" chamber to ensure the chamber and process are functioning as expected and also correct endpoint detection can occur to terminate the process at the desired time. If the plasma state of the process and chamber during processing does not match that of a selected process in a "reference" chamber, a potential fault is detected and the operator is alarmed to take appropriate action. Details of how a chamber and process can be monitored during process to detect endpoint and fault have been disclosed in commonly assigned U.S. Pat. No. 6,368,975, entitled "Method and Apparatus For Monitoring A Process By Employing Principal component Analysis", issued on Apr. 9, 2002 and its divisional application Ser. No. 10/341,696, filed on Jan. 14, 2003.

Besides chamber qualification, process monitoring and endpoint detection, techniques for identifying the source of a chamber fault are also very much in demand. In a semiconductor manufacturing environment, chambers can be found to have insufficient pre-conditioning, such as seasoning, or to have hardware related problems. It's important to quickly determine the sources of the problem (or fault) to reduce the down time of the processing equipment. Extended down time can be very costly.

During a plasma process, certain plasma "attributes", such as the plasma's electromagnetic emissions, the RF power delivered to a wafer pedestal, wafer reflectance, process pressure and process temperature, manifest low frequency fluctuations that contain significant information about the plasma process and the plasma chamber. The intensity of a plasma's optical electromagnetic emission (OES) and the fluctuations of the RF power delivered to a wafer pedestal during plasma processing contain information related to process state, process event and process chamber. OES and RF states are affected to different degrees by varying chamber conditions and by process parameter changes. OES and RF data are complementary to one another. Inclusion of both data during process or chamber monitoring is more comprehensive than merely including one of the two types of data.

Therefore, there is a need in the art for techniques for automatically determining whether a substrate process chamber matches a reference substrate process chamber and the potential source(s) of chamber fault that are repeatable and accurate by comprehensive monitoring of semiconductor plasma processes.

SUMMARY OF THE INVENTION

The invention relates to a method for comprehensive monitoring of semiconductor plasma processes. The invention monitors and compares plasma emission and RF characteristics of a process chamber under test to the plasma emission and RF characteristics of a reference process chamber using a multivariate technique, such as principal component analysis.

Embodiments of the invention provide a method of calibrating a processing chamber. The method includes performing a first substrate processing operation and a first process perturbation operation in a reference chamber, collecting optical emission spectroscopy (OES) data and radio frequency (RF) data during the first substrate processing operation and the first process perturbation operations, performing a multivariate analysis on the collected OES and RF data from the reference chamber, determining if the collected OES and/or RF data need to be manipulated, performing the data manipulation on the OES and/or RF data that were identified to need data manipulation, performing a multivariate analysis on the revised OES and RF data to produce reference multivariate analysis results for the reference chamber, performing a second substrate processing operation and a second process perturbation operation in a process chamber that is under study, where the first process operation and the second operation are similar, and the first process perturbation operation and the second process perturbation operation are similar, collecting OES data and RF data during the second processing operation and the second process perturbation operation, manipulating the OES and/or RF data according to the data manipulation scheme developed for the reference chamber, performing a multivariate analysis on the collected OES and RF data from the chamber under study to produce test multivariate analysis results, comparing the test multivariate analysis results from the chamber under study to the reference multivariate analysis results from the reference chamber, and determining whether the results from the chamber under study match the results from the reference chamber.

In another embodiment of the invention, the results of the comparison can be used for determining the potential source of fault of the chamber under study.

In a further embodiment, the method of the invention uses the results of the comparison for identifying a perturbation parameter that yields results that match poorest with the reference chamber, searching a library for stored diagnosis runs with known faults that have similar OES and RF data as the chamber under study, comparing results of the chamber under study and stored diagnosis runs, and determining whether the results from the chamber under study match the results from the stored diagnosis runs.

BRIEF DESCRIPTION OF THE DRAWINGS

So that the manner in which the features of the invention described herein are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

FIG. 3 shows a graphical output data from an RF detector.

FIG. 5 shows merged data from both RF probe and optical spectrometer for analysis in spectral analysis software.

DETAILED DESCRIPTION

The invention involves measuring correlated attributes of a plasma process in a processing chamber, and by employing principal component analysis to analyze the correlated attributes; process state and chamber state information may be easily and accurately obtained for the process. For convenience, the present invention is described herein primarily with reference to plasma etch processes and plasma-based correlated attributes (e.g., plasma electromagnetic emissions state and RF state). Details of how plasma emission spectrum data can be collected and how principal component analysis can be used to identify principal components have been disclosed in commonly assigned U.S. Pat. No. 6,455,437, entitled "Method and Apparatus For Monitoring The Process State of A Semiconductor Device Fabrication Process, issued on Sep. 24, 2002, U.S. Pat. No. 6,413,867, entitled "Film Thickness Control Using Spectral Interferometry", issued on Jul. 2, 2002, and U.S. Pat. No. 6,368,975, entitled "Method and Apparatus For Monitoring A Process By Employing Principal Component Analysis", issued on Apr. 9, 2002. All of the aforementioned patents are incorporated herein by reference in their entireties. RF power state data, such as RF voltage, current and phase can also be collected in a similar fashion and analyzed together with the OES data. The OES data and RF data are correlated with respect to time.

Figure 1:
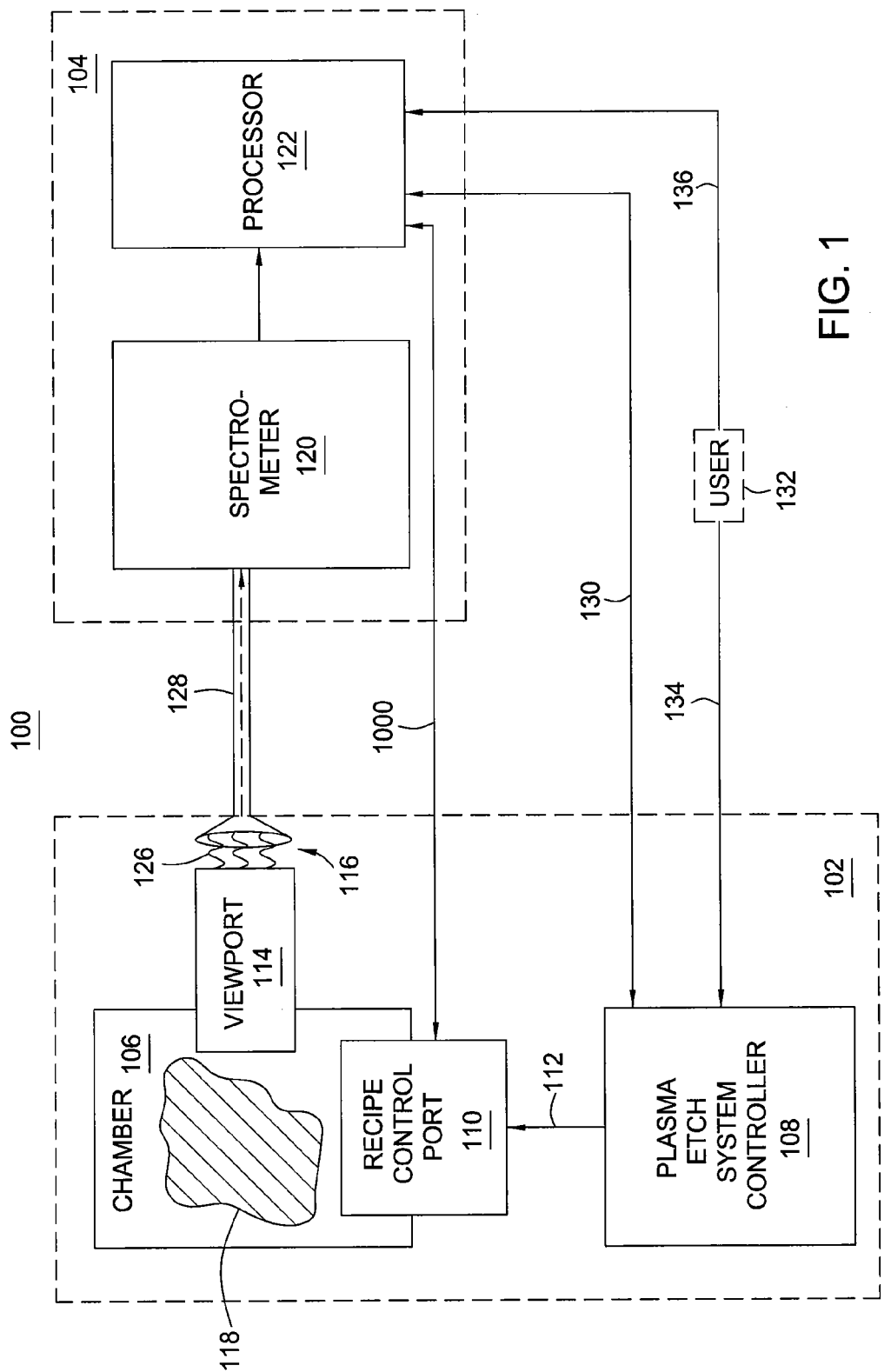
FIG. 1 is a block diagram of a processing system comprising a plasma system and a process monitoring system.

FIG. 1 is a block diagram of a processing system 100 comprising a conventional plasma etching system 102 and a process monitoring system 104 coupled thereto in accordance with the present invention. As used herein, "coupled" means coupled directly or indirectly so as to operate.

The conventional plasma etching system 102 comprises a plasma chamber 106 coupled to a plasma etch system controller 108 via a recipe control port 110 and via a first control bus 112. The plasma chamber 106 comprises a viewport 114 for coupling electromagnetic emissions from the inside of the chamber 106 to the outside of the chamber. The emissions are primarily optical wavelengths within the range from about 180 to 1100 nanometers, generally represented as 116 in FIG. 1. The emissions are produced by plasma 118 sustained within the plasma chamber 106. The plasma electromagnetic emissions 116 comprise emissions from a large number of plasma species (e.g., process gasses, reaction products, etc.) and represent one type of correlated attributes that may be measured for a plasma process. In addition to the plasma electromagnetic emission, the viewport 114 can also be used to collect substrate reflectance of the plasma light or the light from an excitation lamp or laser. Substrate reflectance of the plasma light or the light from an excitation lamp can provide information related to the wafer state. The invention describe here includes the option of collecting substrate reflectance, optical emission, RF, process temperature, and process pressure data. Note that the viewport 114 is shown positioned on the side of the plasma chamber 106, but may be positioned at any other location (e.g., on the top or bottom of the chamber 106) if desired.

The process monitoring system 104 comprises a spectrometer 120 coupled to a processor 122. The spectrometer 120 is positioned to collect the electromagnetic emissions 116 from the plasma 118 and to provide intensity information regarding a plurality of plasma electromagnetic emission wavelengths to the processor 122. A lens 126 and/or a fiber optic cable 128 are disposed between the viewport 114 and the spectrometer 120 for improving collection of the electromagnetic emissions 116 by the spectrometer 120. The processor 122 is coupled to the plasma etch system controller 108 via a second control bus 130.

In operation, a user 132 (e.g., a person in charge of a wafer fabrication process) supplies (via a third control bus 134) the plasma etch system controller 108 with a set of instructions for generating the plasma 118 within the plasma chamber 106 (i.e., a plasma recipe). Alternatively, a remote computer system for running a fabrication process that includes the processing system 100, a manufacturing execution system or any other fabrication control system may supply the plasma etch system controller 108 with a plasma recipe (e.g., as supplied by the user 132 or as stored within a plasma recipe database). A typical plasma recipe includes processing parameters such as the pressure, temperature, power, gas types, gas flow rates and the like used to initiate and maintain the plasma 118 within the plasma chamber 106 during plasma processing. Once the plasma etch system controller 108 receives a plasma recipe from the user 132, from a remote computer system, from a manufacturing execution system, etc., the plasma recipe is supplied to the recipe control port 110 via the first control bus 112, and the recipe control port 110 (or the plasma etch system controller 108 itself if the recipe control port 110 is not present) establishes and maintains within the plasma chamber 106 the processing parameters specified by the plasma recipe.

During a plasma process within the plasma chamber 106, the plasma 118 generates electromagnetic emissions having wavelengths primarily in the optical spectrum (e.g., from about 180 to 1100 nanometers), although both ultra-violet and infrared wavelengths also may result. A portion of these electromagnetic emissions (e.g., the electromagnetic emissions 116) travels through the viewport 114 and reach the inventive process monitoring system 104. Note that while the electromagnetic emissions 116 are represented generally by three emission wavelengths in FIG. 1, it will be understood that the electromagnetic emissions 116 typically comprise many more wavelengths.

With reference to FIG. 1, the spectrometer 120 receives the electromagnetic emissions 116 via the lens 126 and the fiber optic cable 128. In response thereto, the spectrometer 120 spatially separates the electromagnetic emissions 116 based on wavelength (e.g., via a prism or a diffraction grating, and generates detection signals (e.g., detection currents) for a plurality of the spatially separated wavelengths.

Figure 2:
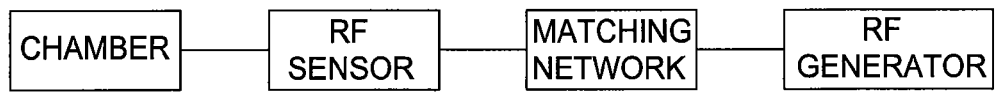
FIG. 2 shows an example of RF sensor placement location.

In addition to monitoring plasma emission wavelengths as correlated attributes of a process, RF state, such as bias voltage, current and phase of a plasma process may be monitored to obtain process state and chamber information. The process monitoring system 104 is adapted to monitor RF power and impedance. Signals representative of the RF power state associated with the plasma chamber 106 during plasma processing are supplied to the processor 122 via a fifth control bus 1000 coupled between the recipe control port 110 and the processor 122. RF data are generally collected by a non-intrusive RF sensor (or detector), which is inserted in the RF power delivery path. An example of the insertion location is between the powered electrode and the impedance-matching network (see FIG. 2). An example of the RF sensor is the Z-SCAN manufactured by Advanced Energy located in Fort Collins, Colo. Z-SCAN has the capability of monitoring voltage, current and phase as well as multiple frequency harmonics up to 90 MHz. As with the plasma emission fluctuations, the processor 122 examines over time local frequency changes in the RF power and impedance detection signals. Specifically, the RF power and impedance detection signals are periodically sampled via the processor 122.

The collected emission wavelengths and RF signals represent correlated attributes of the plasma process that may be analyzed via principal component analysis. The particular type of processing to be performed by the processor 122 is selected by the user 132 (or by a remote computer system, by a manufacturing execution system, etc.) via a fourth control bus 136.

Figure 4:
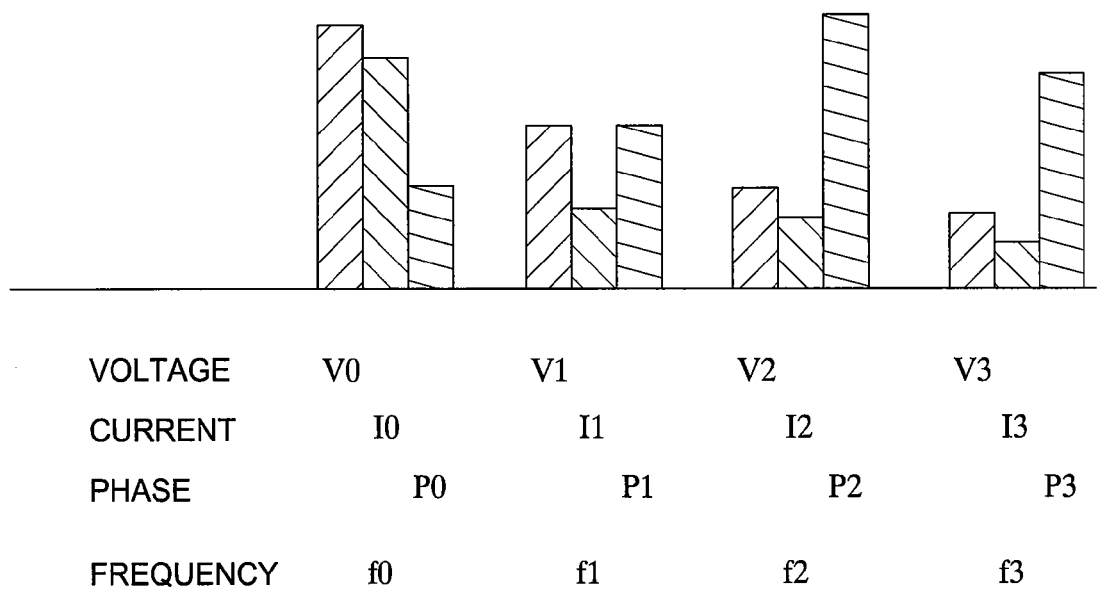
FIG. 4 shows a graphical output data from optical spectrometer.

FIG. 3 is a plot of an output from an optical spectrometer. The plot depicts optical signal intensity as a function of wavelength at a particular moment in time. FIG. 4 shows a plot of an output from an RF sensor, which collects voltage (V), current (I) and phase (P) under various frequencies f0, f1, f2, and f3 at the same particular moment as FIG. 3 (correlated data). FIG. 5 shows how the optical spectrometer data can be merged with the correlated RF data. The RF data can be appended on either side of the optical spectra data. The correlated data can be collected within selected time period during processing.

RF state data provide additional plasma state information that is complementary to the OES data. In one embodiment of the invention, OES data and RF data are collected during a polysilicon etching process before perturbation of a process being performed by a chamber and after the perturbed process has reached steady state. In one embodiment of the invention, the process parameters that are perturbed include: source power, bias power, chamber pressure, $O_2$ flow rate, HBr flow rate and $Cl_2$ flow rate. The perturbation amount is 10%. Principal component analysis (PCA) is performed on the averaged OES signals and RF data before and after perturbation to find two most important steady (state) principal components (PCs), PC1 and PC2. The decomposition of the data matrix yields scores for the two principal components. The scores represent the coefficients of the principal components and indicate the divergence from the un-perturbed process. Score "0" reflects the normal, un-perturbed process; therefore, the normal process has PC1 and PC2 scores of to be (0,0).

PCA is a multivariate technique which transforms a number of correlated variables to a smaller set of uncorrelated variables or factors that describe the major variation in a data set. An example of data matrix $X_{m \times n}$ is composed of m samples (rows), taken at $t_1$, $t_2$ to $t_m$, and n variables (columns), including OES intensities at various wavelengths and RF measurements at various frequencies. An example of the plasma monitoring by EyeD product of Applied Materials, which includes 1201 OES data channels (between 200 to 800 nm wavelengths) and 60 RF data channels to sample voltages, currents and phases under different frequencies. The signals can be sampled at 10 times per second. The columns of X are usually normalized to zero man and unit variance.

$$X_{m \times n} = X_{11}, X_{12}, \ldots, X_{1n}$$
$$X_{21}, X_{22}, \ldots, X_{2n}$$
$$X_{m1}, X_{m2}, \ldots, X_{mn} \quad (1)$$

Principal components are the eigenvectors of matrix $X^T X$. The columns of V are the eignvectors and the diagonal elements of $\Omega$ are the eigenvalues.

$$X^T X = V \Omega V^T \quad (2)$$

The data matrix $X_{m \times n}$ can be decomposed into a score matrix T (orthogonal) and a loading matrix P (orthonormal) plus a residual matrix E. The score matrix contains information on how the samples related to one another, while the loading matrix contains information on how variables related to one another.

$$X_{m \times n} = T_{m \times l} P^T_{n \times l} + E_{m \times n} \quad (3)$$

The abnormal changes in a sample can be detected by monitoring its scores and the values of the sum of squares of each row of E (residual matrix) (called Q) and the sum of the normalized squared scores (called $T^2$). A9

Figure 6A:
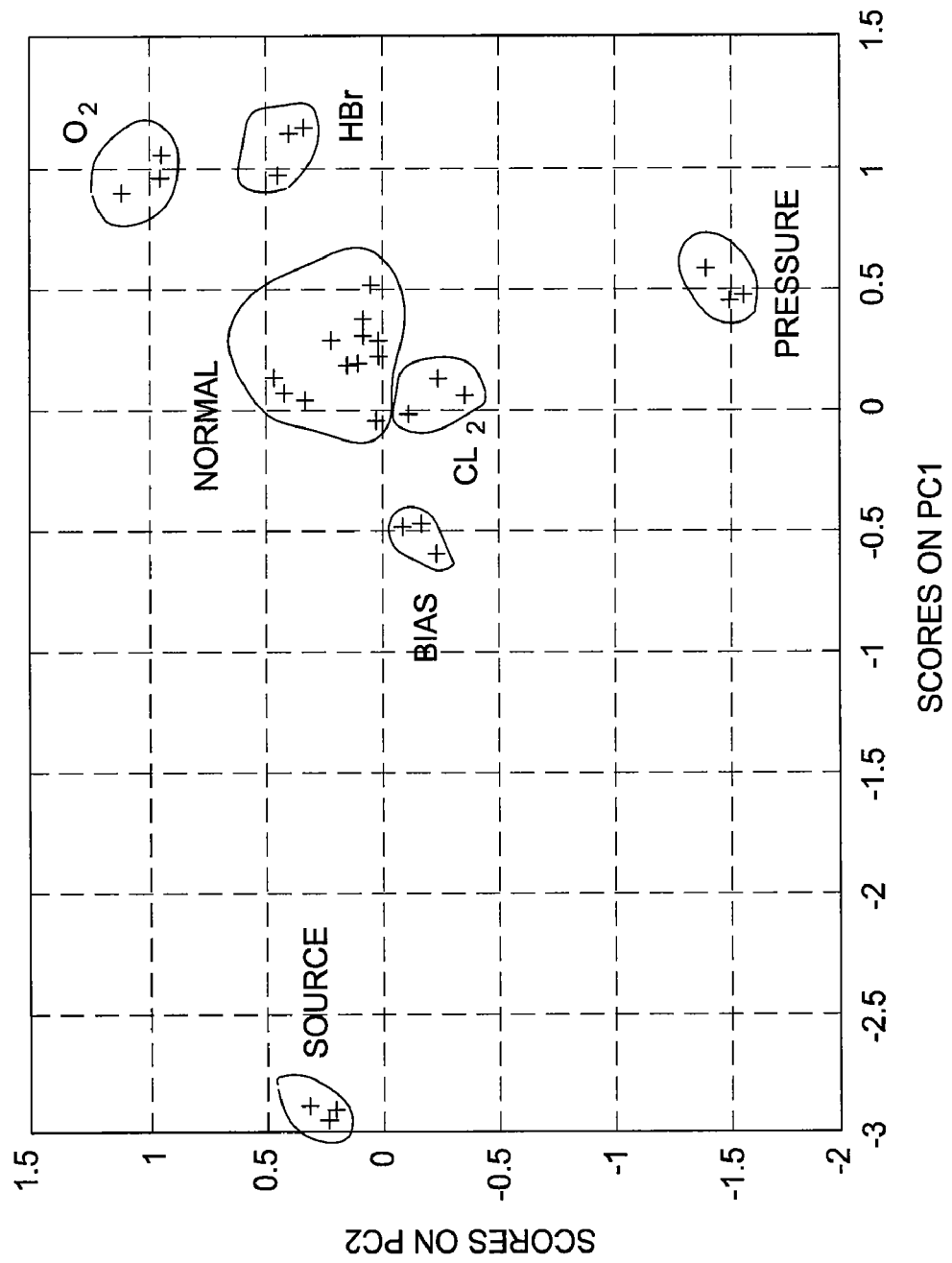
FIGS. 6A and 6B are steady state scores of PC1 and PC2 for various chamber perturbations for averaged OES data (6A) and RF data (6B).
Figure 6B:
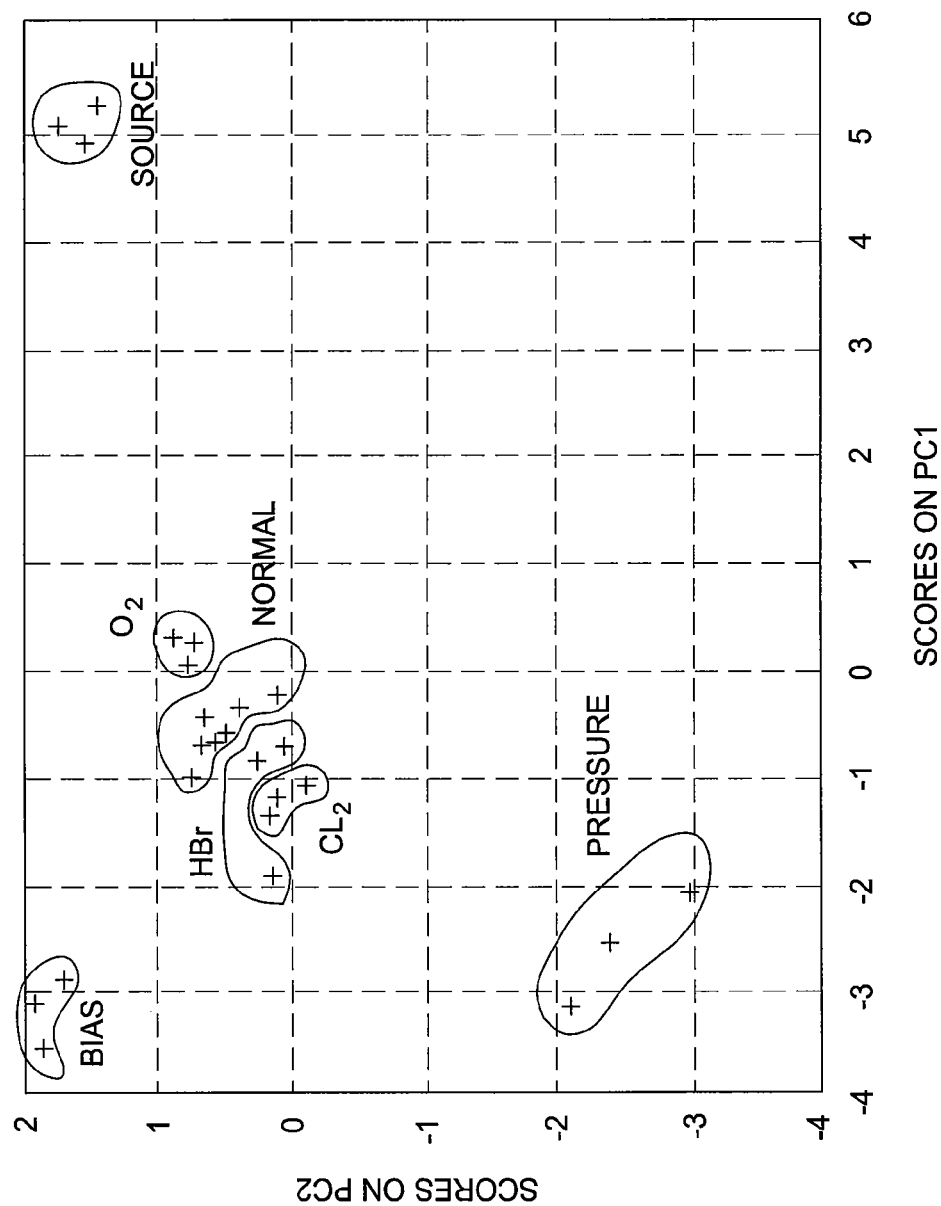

FIGS. 6A and 6B are plots of scores of principal components 1 and 2 as collected during etch chamber qualification. FIG. 6A is for OES analysis and FIG. 6B is for RF analysis. FIG. 6A shows that the perturbation of source power, chamber pressure and $O_2$ flow rate greatly affect the OES state; while FIG. 6B shows that source power, chamber pressure and bias power significantly affects the RF state. Perturbation of source power and perturbation of chamber pressure both greatly affect the OES and RF states. While perturbation of the $O_2$ flow rate affects the OES state more than the RF state and perturbation of the bias power affects the RF state more than the OES state. HBr and $Cl_2$ perturbation have weak effects on the OES and RF data. When the OES data and RF data are found not to correlate, such as $O_2$ flow rate and bias power perturbation in this example, or weak effects on OES and RF data by the perturbation, such as HBr and $Cl_2$ flow rate, signal enhancement of the data or selecting a narrower and more sensitive signal range of wavelength (for OES) and frequency (for RF) could be considered to ensure detection of process parameter variation.

Besides OES and RF reacting differently to different process parameter perturbations, RF data (or OES data) could be more discernible than the OES data (or RF data) in some instances. For example, during contact or via etch; the percentage of the open area is quite small. It could be as low as 1%. Under such circumstance, RF signals would correlate better with process and chamber changes, because optical emission signals that result from etch byproducts from 1% opening would be relatively weak. This shows that the information provided by OES and RF data are complementary. It's important to include both sets of data in any analysis of the chamber operation.

Figure 7:
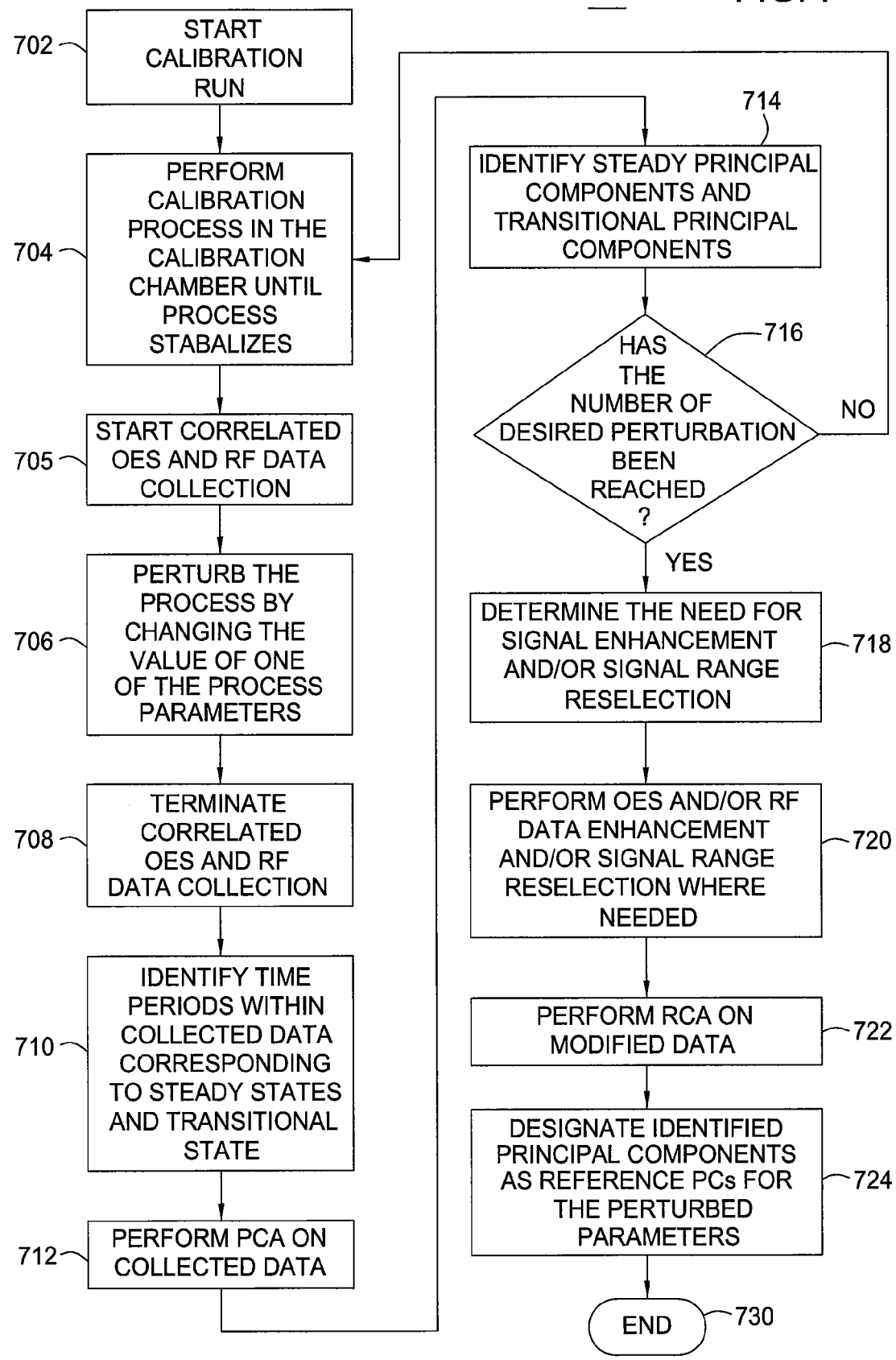
FIG. 7 is flow charts illustrating the steps involved in calibration processes according to an embodiment of the present invention that uses principal component analysis (PCA).

As mentioned above, techniques for comprehensive calibration of a "reference" chamber for qualification of a chamber newly manufactured or newly maintained are needed for improved process repeatability and control. FIG. 7 is a flowchart illustrating the steps involved in a calibration process 700 according to an embodiment of the present invention that uses principal component analysis (PCA) techniques. As previously mentioned, other embodiments of the invention may employ multivariate techniques other than PCA techniques. As shown in FIG. 7, calibration process 700 starts at step 702 by running a calibration process in a reference chamber until the process stabilizes (or reaches steady state) at step 704. The reference chamber forms a reference chamber having an ideal function. At step 705, the process 700 begins collecting the correlated OES and RF data. Then, at step 706, the process is perturbed by changing the value of one of the process parameters. In the case of polysilicon etch, the parameters could include, but are not limited to: source power, bias power, chamber pressure, $O_2$ flow rate, HBr flow rate, and $Cl_2$ flow rate. The amount of change should not be too much that the process is substantially impacted (for example, less than 50%). Typically, the amount is less than 20% and preferably less or equal to 10%. The change could be positive or negative, which means that the value of the parameter can either be increased or decreased. The perturbed process will eventually reach a steady state. Correlated attributes of plasma OES data and RF data (correlated with time) are collected (at step 708) for the entire process. At step 708, the data collection is terminated.

Figure 8A:
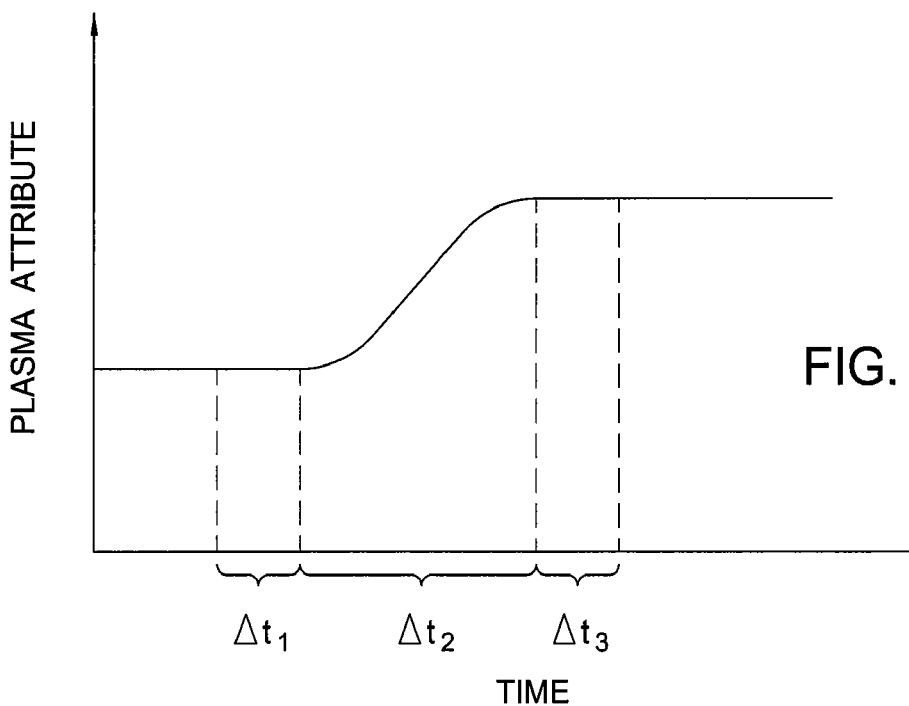
FIGS. 8A and 8B are schematic plots of the value of a plasma attribute as a function of time before perturbation and after perturbation for a simple transition example (8A) and for a more complicated transition example (8B).
Figure 8B:
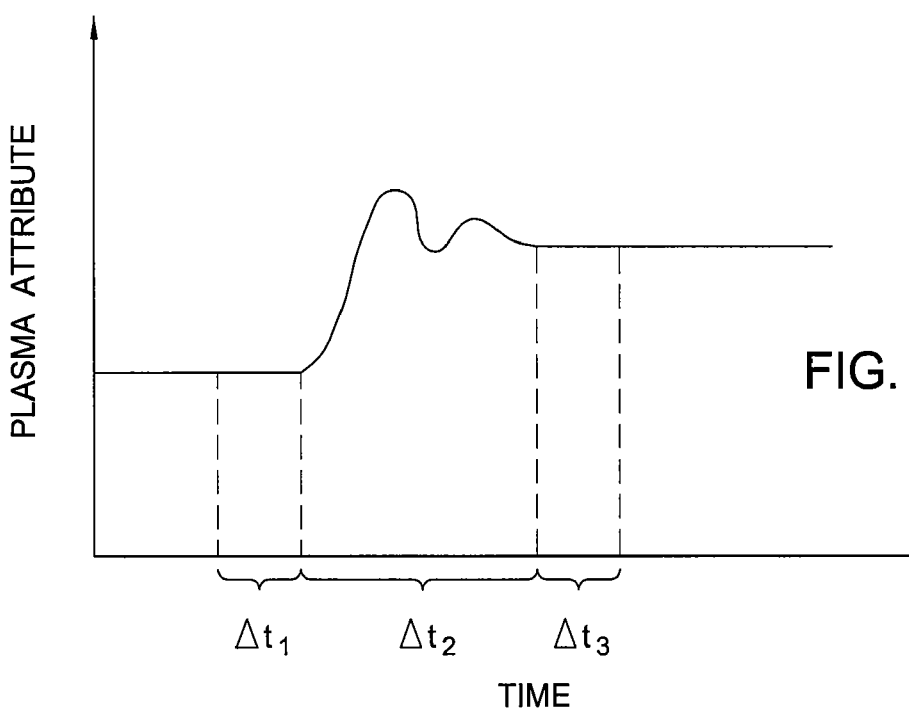

At step 710, two periods ($\Delta t1$ and $\Delta t3$, see FIGS. 8A and 8B) are identified within the collected data that correspond to the steady states of the process (before perturbation and after perturbation). One period ($\Delta t2$, see FIGS. 8A and 8B) of time is identified within the collected data that correspond to the transitional state of the process. A window of data for a number of different sample times (selected within the time periods, typically evenly sampled within the period) can be examined. The number of sample times within the transitional period ($\Delta t2$) depends on the transitional state. If the transitional state is simple (FIG. 8A), the number of sample times is small. If the transitional state is more complex (FIG. 8B), the number of sample times is large to ensure sufficient samples of data track the transitional state. The collected data within the window is used to form a matrix having rows comprising the measured correlated attribute data and the columns comprising the time each attribute set was measured. The data within the matrix is mean centered so that singular value decomposition can be performed on the matrix and principal component eigenvectors are generated for the collected data within the matrix.

At step 712, principal component analysis (PCA) is performed on the collected data for the calibration process. At step 714, the principal components (PCs) for steady state and transitional state are identified for the process and the reference chamber. Additional perturbation processes can be conducted to collect more principal components until desired number of perturbation processes is reached. The method queries at step 716 whether the number of desired perturbations have been performed. If the query is negatively answered, the method proceeds to step 704. If the query is affirmatively answered, the method stops at step 726.

The calibration process illustrated can be improved by enhancing signals or by selecting a narrower and more sensitive signal range for the perturbation parameters that yielded weak effects on OES and RF data. It was shown earlier in FIGS. 6A and 6B that some perturbation parameters, such as $O_2$ flow rate, bias power, HBr flow rate, and $Cl_2$ flow rate, yielded weak effects on either OES data or RF data, or both OES and RF data. For these parameters, signal enhancement or selection of a narrower and more sensitive signal range can be included to ensure detection of changes in the parameter values. The need for signal enhancement or selection of a narrower and more sensitive signal range can be determined by decomposition of the OES and RF data matrix (step 718) for the principal components. An example has been shown in FIGS. 6A and 6B. Perturbation parameters that yielded weak effects can be identified. The weak signals could be enhanced by amplifying post perturbation signals or a narrower and more sensitive wavelength range (narrower than 200-800 nm) or frequency range could be reselected (step 720) to magnify the change. Once the degree of signal enhancement is determined during the chamber calibration run, the same degree of signal enhancement should be performed on the OES and RF data collected during chamber study run. PCA should be performed again (step 722) on the data that have been enhanced or reselected to identify steady and transitional principal components again. At step 724, final sets of principal components would be designated as reference steady (state) principal components (RSPC) and reference transitional (state) principal components (RTPC) for the "reference" chamber and perturbation parameters. The number of sets of RSPC and RTPC corresponds to the number of perturbation parameters.

Figure 9:
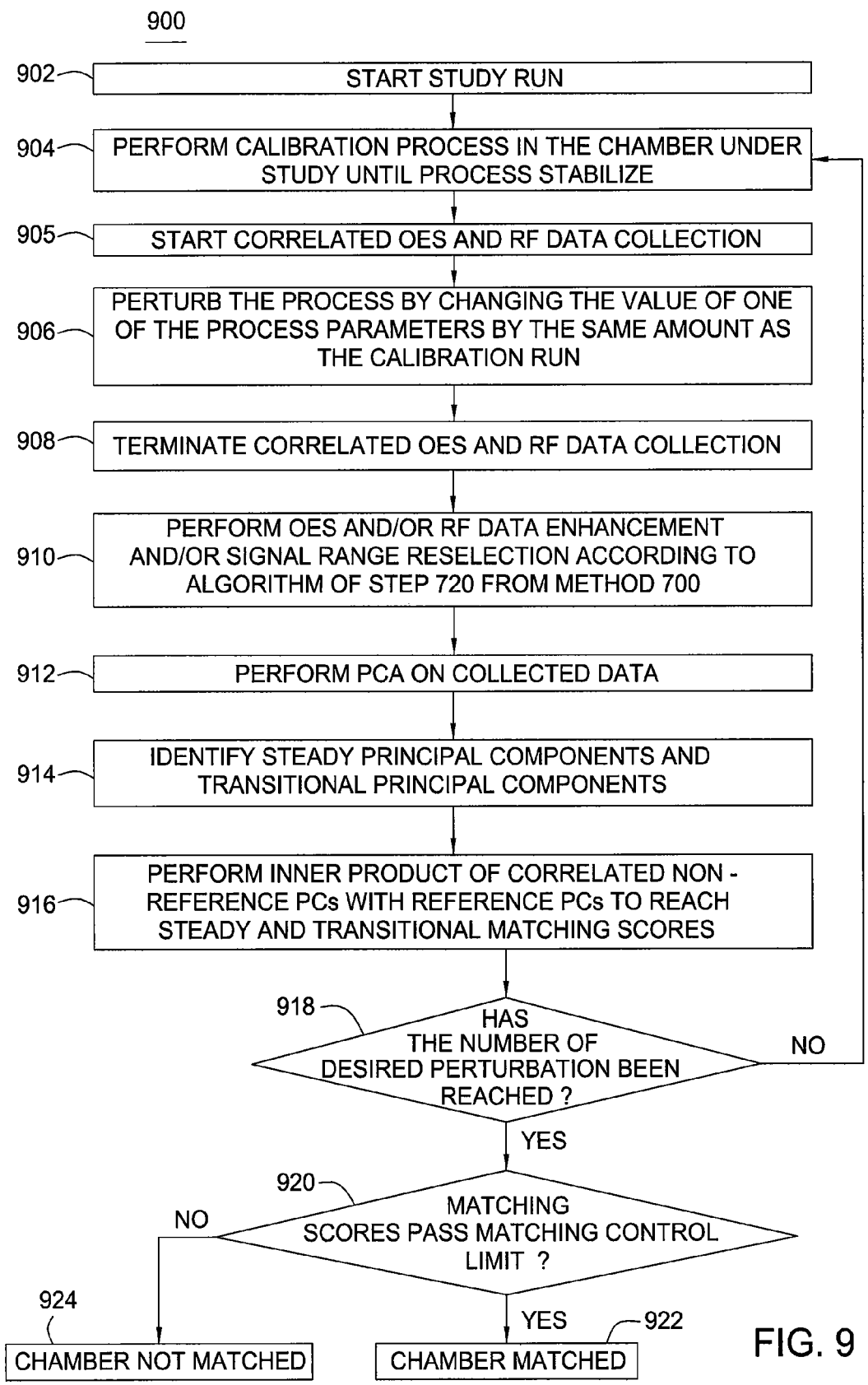
FIG. 9 is a flow chart illustrating the steps of a method for determining the matching of a substrate process chamber to a calibration substrate process chamber.

FIG. 9 depicts a flow diagram of a method 900 of the operation of a chamber under study in accordance with the present invention. Once the reference principal components for the reference chamber and calibration process are generated by method 700, the method 900 performs process runs in the chamber that needs to be qualified or matched. The chamber could be a chamber in the chamber manufacturing area that needs to be qualified, a chamber that needs to be started up in a new fab or a chamber that has recently undergone some regular maintenance, such as wet clean. The "study runs" begin at step 902. Process and process sequences are run in the chamber under study at steps 904 and 906 that are identical to the processes run in the reference chamber at steps 704 and 706. At step 905, identical data collection procedures (same as step 705) are used and correlated attributes with the identical measurement times for similar processes are collected. The data collection terminates at step 908. At step 910, the OES and RF signals would be enhanced or signal range be reselected according to the algorithm developed at step 720 of method 700. At step 912, PCA is performed on these collected correlated attributes and, at step 914; the method identifies steady (state) principal components SPC and transitional (state) principal components TPC for the chamber under study.

At step 916, the steady and transitional principal components (SPC and TPC) of the chamber under study are compared against correlated reference steady and transitional principal components (RSPC and RTPC) of the reference chamber by forming inner products of the correlating eigenvectors (or principal components). The resulting values of the inner products are between −1 and 1, with 1 giving a perfect process match, 0 gives no process match, while −1 give an opposite reaction to the process perturbation. The resulting values provide "matching" steady and transitional scores for the chamber under study.

At step 918, the method 900 queries whether the desired number of perturbations has been used to produce SPC and TPC. If the query is negatively answered, the method 900 returns to step 904 to collect data for a new perturbation. If the query is affirmatively answered, the method proceeds to step 920.

At step 920, the method queries whether the matching scores pass a matching score control limit. If the query is negatively answered, the method 900 deems that the chamber under study does not match the reference chamber. If the query is affirmatively answered, the method 900 deems the chamber under study matched to the reference chamber.

Figure 10:
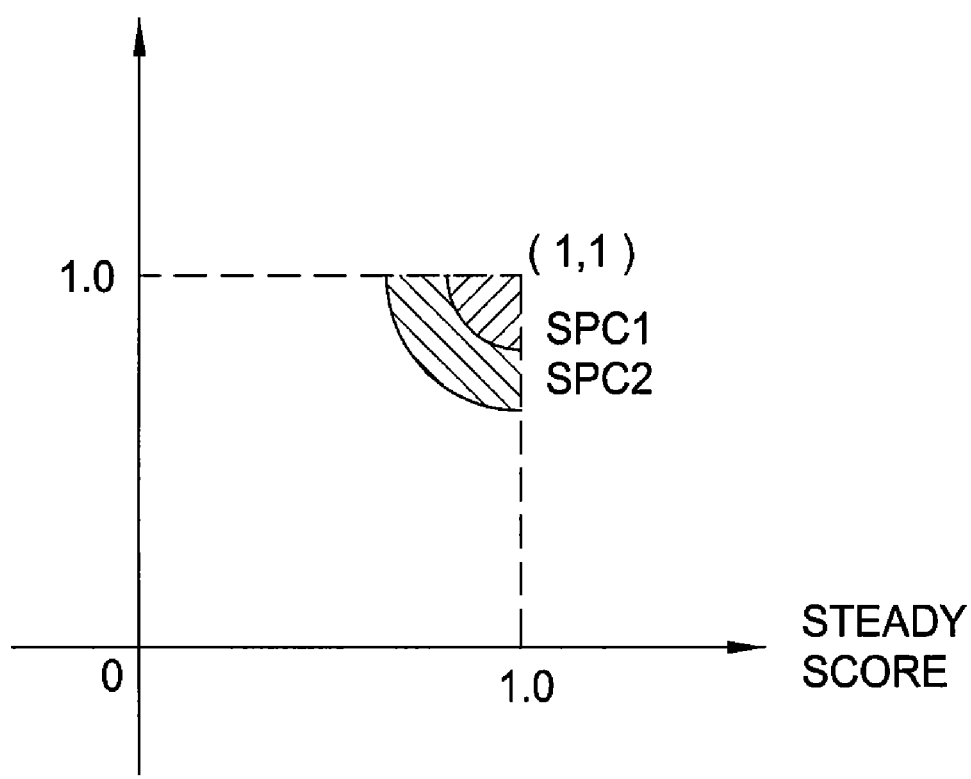
FIG. 10 is a chamber matching score chart for a chamber with a calibration process that has only a steady score and a transitional score.

FIG. 10 is a diagram of a simplified case that has only one steady principal component and one transitional principal component for a process parameter perturbation. An ideal "matched" chamber should have steady score and transitional score both at 1. Statistic process control limits (SPC1, SPC2) can be established to determine whether the chamber under study pass the criteria. The statistic process control limits can be of other shapes. They define the boundaries of "matching" scores for the process chamber to be considered matched. For a complete chamber matching, typically more than one process parameter perturbation would be conducted. Multiple chamber matching control graphs similar to FIG. 6 would be needed and used.

In a production environment, if a substrate process chamber shows signs of process drifting, or otherwise operating in a faulty manner, the wafer processing would need to be immediately stopped to ensure that incorrect processing does not affect many wafers. The source of the chamber fault would need to be quickly diagnosed such that cause(s) of the fault can be repaired and the chamber restarted. Suppose the source of chamber fault is low source power, traditional diagnosis would require a technical expert to review the data log and then propose possible causes. It will take from a few hours to a couple of days to identify the problem source. Using the present invention, the system can be instructed to trigger a series of diagnosis perturbation runs that are similar to chamber matching. The OES and RF signals generated from these diagnosis runs can be compared against the OES and RF data generated from process parameter perturbation tests performed in a reference chamber in a fashion similar to chamber matching. Using the example above, the matching score for the source power perturbation run would be low and would give an equipment expert or operator a lead for further investigation. The whole perturbation process, data collection and data analysis are all done automatically and would take the most a couple of hours, which is much faster than a manual process.

Figure 11:
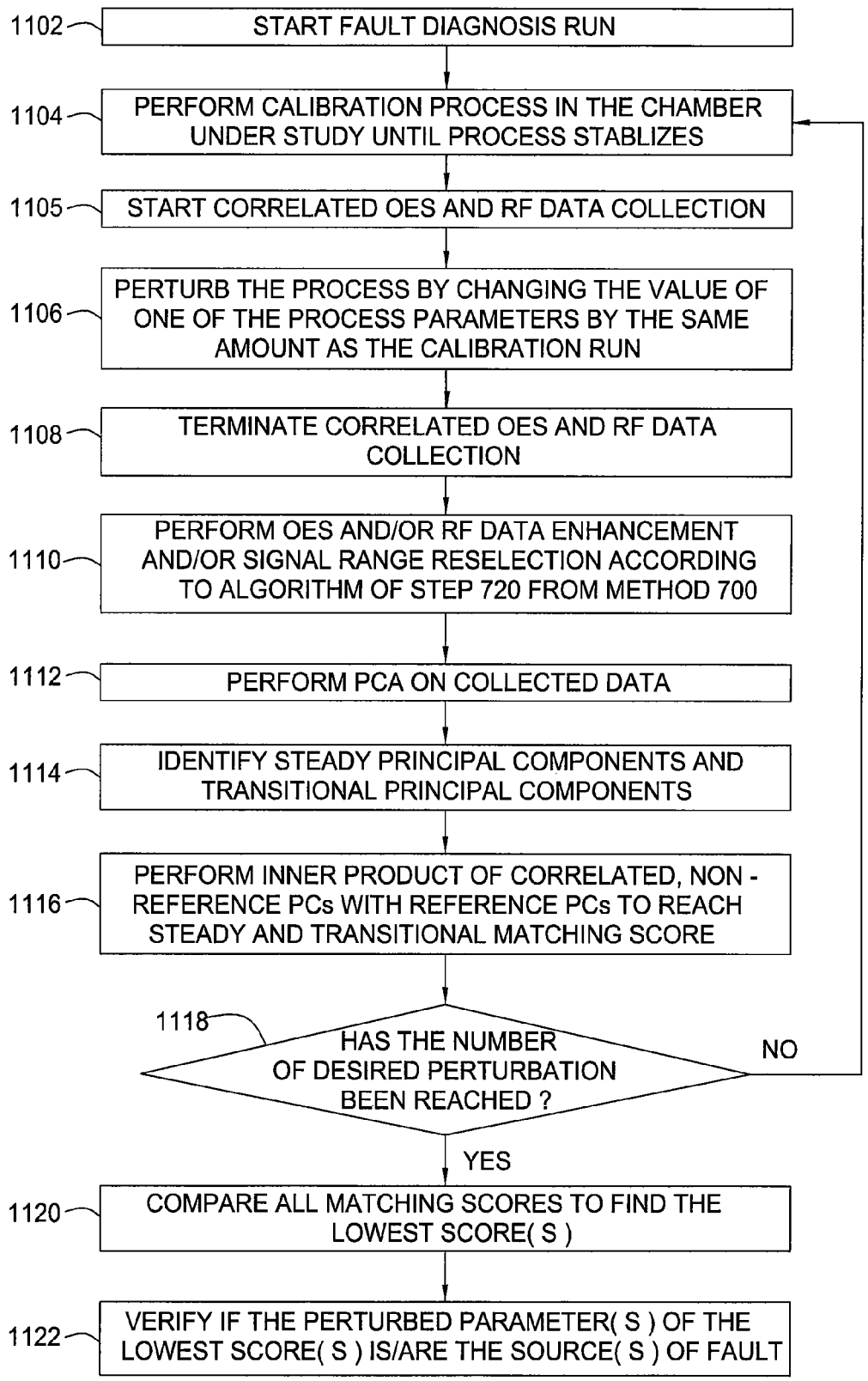
FIG. 11 is a flowchart illustrating steps of a method of diagnosing the source(s) of chamber fault.

FIG. 11 depicts the process flow of a method 1100 for chamber fault diagnosis. At steps 1104 and 1106, process and process sequences are run in the chamber under study that are identical to the processes run in the reference chamber. At steps 1105 and 1108, identical data collection procedures are used and correlated attributes with the identical measurement times for similar processes are collected. At step 1110, the OES and RF signals would be enhanced or signal range be reselected according to the algorithm developed at step 720 of method 700. At step 1112, PCA is performed on these collected correlated attributes. At step 1114, the method 1100 identifies steady (state) principal components SPC and transitional (state) principal components TPC for the chamber under study.

At step 1116, the steady and transitional principal components (SPC and TPC) of the chamber under study are compared against correlated reference steady and transitional principal components (RSPC and RTPC) of the reference chamber by forming inner products for the correlating eigenvectors (or principal components). Via query 1118, the method 1100 may perform further data collection using other perturbation of process parameters. The resulting values from the inner products provide "matching" scores for the chamber under study. Once the matching scores for all perturbation runs are collected, at step 1120, the matching scores are compared. The perturbation parameter(s) that yields the lowest matching scores can be identified. At step 1120, the possible source(s) of fault is related to the perturbation. For example, if the matching scores were low for the flow rate perturbation of one of the reactive gas, one would check the gas flow controller, calibrate the mass flow meter or check the fullness of the gas tank.

Past fault diagnosis runs with known faults could be very useful in fault diagnosis. The principal components of the current diagnosis runs can be compared with the principal components of past fault diagnosis that are stored in the memory. If there are good matches of the principal components, the source of fault can be identified, which would result in reducing the amount of work associated with pinpointing the source of fault.

Figure 12:
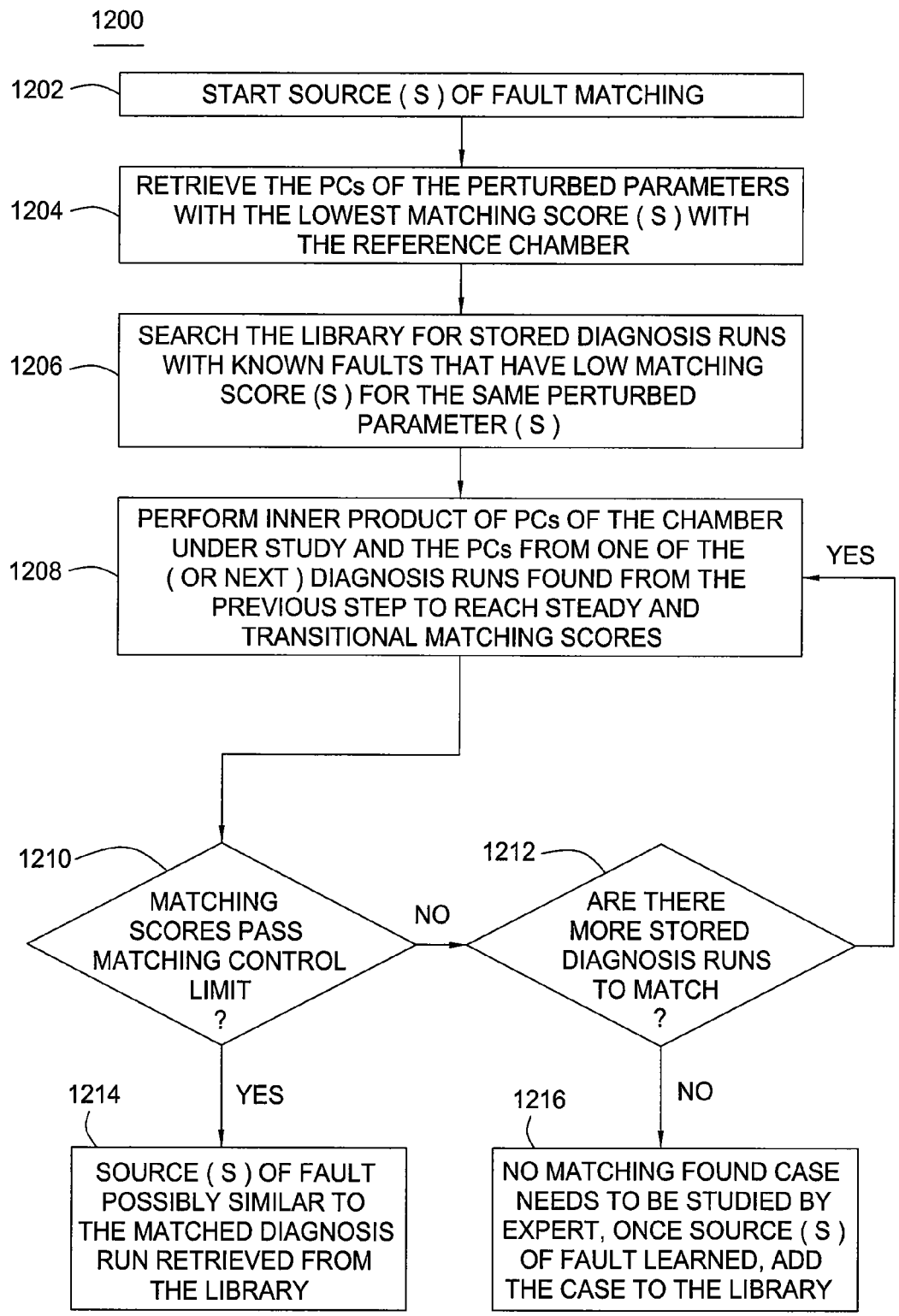
FIG. 12 is a flowchart illustrating steps of a method of matching the principal components of a faulty chamber with stored principal components data collected from chambers with known faults.

FIG. 12 shows the process flow of a method 1200 that identifies the source(s) of a fault 1200. The method 1200 begins at step 1202 and proceeds to step 1204 where the system retrieves the principal components that have the lowest matching scores with respect to the reference chamber. The method 1200, at step 806, searches the library (or memory) for past diagnosis runs with known faults that have low matching score(s) for the same perturbed parameter(s). At step 1208, inner product computations of the correlated principal components are performed to obtain matching scores. A control limit can be established to determine if the principal components of the chamber under study sufficiently matches the principal components of the chamber with known fault. At step 1210, the method 1200 queries whether the matching scores pass a matching control limit. If the query is affirmatively answered, the method 1200, at step 1214, deems the fault retrieved from the memory to be a possible fault source for the chamber under study. If the query of step 1210 is negatively answered, the method proceeds to step 1212 where the method queries if additional diagnosis runs are available for comparison. If they are available, the method returns to step 1208 to process the next diagnosis run. If no other diagnosis runs are available, the method 1200 proceeds to step 1216. At step 1216, if no matching can be found with the known faults stored in the library, the case needs attention from experts. Once the source of fault is identified by the expert, the principal components, the matching scores, and the source of fault can be stored in the library for future diagnosis.

Accordingly, while the present invention has been disclosed in connection with various embodiments thereof, it should be understood that other embodiments might fall within the spirit and scope of the invention, as defined by the following claims.

What is claimed is:

1. A method of evaluating a processing chamber, comprising:
   performing a substrate processing operation and a process perturbation operation in a process chamber;
   collecting optical emission spectroscopy (OES) data and radio frequency (RF) data during the substrate processing operation and the process perturbation operations; and
   performing a multivariate analysis on the collected OES and RF data from the process chamber; wherein the process perturbation operation includes a perturbation of at least one of source power, bias power, chamber pressure and gas flow.

2. The method of claim 1, wherein the multivariate analysis comprises principle component analysis (PCA).

3. The method of claim 2, further comprising:
   determining if the OES and/or RF data need to be manipulated;
   performing the data manipulation; and
   performing a multivariate analysis on the revised OES and RF data from the chamber.

4. The method of claim 3, wherein steady principle components and transitional principle components are identified for the process chamber by principle component analysis.

5. The method of claim 3, further comprising:
   using decomposition of an OES and RF data matrix to yield scores of principal components to determine if the OES and/or RF data need to be manipulated.

6. The method of claim 3, further comprising:
   enhancing the weak signals either by amplifying post perturbation signals prior to a substrate processing operation, or by selecting a narrower and more sensitive wavelength range or frequency range.

7. The method of claim 1, further comprising:
   using a result of the multivariate analysis to calibrate the process chamber or calibrate another process chamber.

8. The method of claim 1, further comprising:
   using a result of the multivariate analysis to identify a fault in the process chamber or identify a fault in another process chamber.

9. A method of evaluating a processing chamber, comprising:
   collecting optical emission spectroscopy (OES) data and radio frequency (RF) data from a processing chamber during a substrate processing operation and a process perturbation operation; and
   determining if the collected data meets a predefined process window; wherein the process perturbation operation includes a perturbation of at least one of source power, bias power, chamber pressure and gas flow.

10. The method of claim 9, wherein determining further comprises:
    performing a multivariate analysis on the collected OES and RF data.

11. The method of claim 9, wherein collecting further comprises:
    establishing a baseline characteristic of the processing chamber from the collected OES and RF data.

12. The method of claim 11, wherein determining further comprises:
    comparing a second set of OES and RF data collected from processing chamber the baseline.

13. The method of claim 9, wherein determining further comprises:
    comparing the data collected from processing chamber to OES and RF data collected from a reference processing chamber.

14. The method of claim 9, wherein determining further comprises:
    determining a source of a fault from the collected OES and RF data.

15. The method of claim 9 further comprising:
    comparing the collected OES and RF data to OES and RF data collected from another processing chamber.

* * * * *

UNITED STATES PATENT AND TRADEMARK OFFICE
CERTIFICATE OF CORRECTION

PATENT NO. : 7,695,987 B2  
APPLICATION NO. : 11/612961  
DATED : April 13, 2010  
INVENTOR(S) : Davis et al.

Page 1 of 2

It is certified that error appears in the above-identified patent and that said Letters Patent is hereby corrected as shown below:

Column 1, Lines 43-60, please delete paragraph

"To ensure that a correct amount and quality of film is deposited or etched, substrate processing in a process chamber needs to be monitored during the processing. Plasma state of the process and chamber during processing needs to match that of a selected process in a "reference" chamber to ensure the chamber and process are functioning as expected and also correct endpoint detection can occur to terminate the process at the desired time. If the plasma state of the process and chamber during processing does not match that of a selected process in a "reference" chamber, a potential fault is detected and the operator is alarmed to take appropriate action. Details of how a chamber and process can be monitored during process to detect endpoint and fault have been disclosed in commonly assigned U.S. Pat. No. 6,368,975, entitled "Method and Apparatus For Monitoring A Process By Employing Principal component Analysis", issued on Apr. 9, 2002 and its divisional application Ser. No. 10/341,696, filed on Jan. 14, 2003."

and insert paragraph

--To ensure that a correct amount and quality of film is deposited or etched, a process chamber needs to be monitored and be compared to a "reference" chamber ("good" chamber or "golden" chamber). The procedure used to compare chambers is sometimes called chamber qualification. Chamber qualification procedures are used at various times during a chamber's use. When a process chamber is newly manufactured, the chamber must be qualified. The new chamber needs to be matched to a "golden" chamber to ensure the new chamber will perform according to its specification. Once the chamber is qualified, the chamber can then be shipped to a semiconductor manufacturing facility. Once the chamber arrives at the semiconductor manufacturing facility, the chamber is reassembled and "qualified" again prior to processing the production materials. In addition, in a semiconductor manufacturing facility, a plasma deposition or etching chamber can potentially be used to run different process recipes for different substrates. Before a process recipe is changed, the chamber usually needs to be "qualified" again to ensure the chamber is operating normally before the process recipe change occurs. Lastly, production chambers must undergo regular Signed and Sealed this  
Eighth Day of May, 2012

David J. Kappos  
*Director of the United States Patent and Trademark Office* maintenance or cleaning. After maintenance or chamber cleaning, the chamber needs to be "qualified" again prior to running production wafers. For new generation semiconductor manufacturing, stringent chamber matching techniques that utilize comprehensive plasma monitoring are needed to ensure process repeatability and control.-- therefor;

Column 7, Line 2, please delete "A9"